(12) United States Patent
Babb

(10) Patent No.: US 7,150,108 B2
(45) Date of Patent: Dec. 19, 2006

(54) OBSTETRIC CALIBRATION GUIDE

(76) Inventor: Pamela E. Babb, 5807 S. Cree Dr., Spokane, WA (US) 99206

( * ) Notice: Subject to any disclaimer, the term of this patent is extended or adjusted under 35 U.S.C. 154(b) by 0 days.

(21) Appl. No.: 10/912,628

(22) Filed: Aug. 5, 2004

(65) Prior Publication Data

US 2006/0026854 A1    Feb. 9, 2006

(51) Int. Cl.
*A61B 5/103* (2006.01)
*A61B 5/107* (2006.01)
*G01B 3/10* (2006.01)

(52) U.S. Cl. ............................ 33/563; 33/562; 33/511; 33/512; 600/591; 600/587

(58) Field of Classification Search ................. 33/563, 33/562, 566, 511, 512, 514.1, 555.1, 555.2; 600/591, 587, 588, 304, 551, 38

See application file for complete search history.

(56) References Cited

U.S. PATENT DOCUMENTS

| | | | | |
|---|---|---|---|---|
| 1,062,525 A | * | 5/1913 | Ward | 33/555.2 |
| 2,394,140 A | * | 2/1946 | Biscow | 606/119 |
| 2,478,071 A | * | 8/1949 | Agrillo | 33/565 |
| 2,500,873 A | * | 3/1950 | Sager | 33/563 |
| 3,090,533 A | * | 5/1963 | Claeys et al. | 223/35 |
| 3,643,651 A | * | 2/1972 | Cuadros | 600/591 |
| 4,245,656 A | * | 1/1981 | Farr et al. | 600/588 |
| 4,719,925 A | * | 1/1988 | Parsons | 600/588 |
| 5,511,316 A | * | 4/1996 | Fischer et al. | 33/1 F |
| 5,577,328 A | * | 11/1996 | Kerry, Sr. | 33/563 |
| 5,807,281 A | * | 9/1998 | Welch | 600/588 |
| 6,066,104 A | * | 5/2000 | Dao et al. | 600/588 |
| 6,216,354 B1 | * | 4/2001 | Carbone | 33/565 |
| 6,286,224 B1 | * | 9/2001 | Lewis | 33/562 |
| 6,321,457 B1 | * | 11/2001 | Lariviere et al. | 33/562 |
| 2004/0260207 A1 | * | 12/2004 | Eini et al. | 600/587 |

OTHER PUBLICATIONS

Applicant submits a photograph of a Ross Laboratory Cervical Dilation Poster. Publication date unknown.
Appliant submits a calibration guide developed and tested by Applicant in hospital delivery rooms beginning in the 1990's. Applicant requests return of specimen.

* cited by examiner

*Primary Examiner*—G. Bradley Bennett
*Assistant Examiner*—Amy R. Cohen
(74) *Attorney, Agent, or Firm*—Lee & Hayes, PLLC

(57) ABSTRACT

The described embodiments relate to cervical calibration guides. One such guide includes a gripable structure, and multiple reference structures. Individual reference structures have a deflectable region and a hinge region. The hinge regions of individual reference structures are joined with the gripable structure.

10 Claims, 10 Drawing Sheets

OBSTETRIC CALIBRATION GUIDE

BACKGROUND

Obstetrics utilizes various physical examinations to assess a patient during pregnancy. Such physical examinations can include, among others, examining the cervical dilation, and examining the conjugate diameter of the pelvic opening. As a pregnancy culminates in labor and delivery, physical examination of the cervix contributes to proper patient diagnosis. As a result, many tools have been developed to aid in such examinations. Despite these developments, many cervical examinations continue to be achieved with nothing more than a blind digital exam using an ubiquitous surgical glove worn upon a caregiver's hand.

BRIEF DESCRIPTION OF THE DRAWINGS

The same numbers are used throughout the drawings to reference like features and components wherever feasible. The various components described below may not be illustrated to scale. Rather, the included figures are intended as diagrammatic representations to illustrate to the reader various inventive concepts that are described herein.

DETAILED DESCRIPTION

Overview

The following relates to a calibration guide or apparatus for use in assessing physical measurements of a patient during pregnancy, such as during labor and delivery. In some embodiments, the calibration guide can comprise a tactilely-resistant, cervix-approximating reference structure. Further, in some embodiments, the calibration guide may comprise a resilient digital dilation guide which is used externally of, and not internally of the patient.

A caregiver may utilize the calibration guide to assess the patient's physical condition upon completion of a physical exam. For example, the caregiver may conduct a digital cervical exam where the caregiver's fingers tactilely engage the patient's cervix. The caregiver may then tactilely engage the calibration guide to provide calibrated reference dimensions. The calibration guide may in some embodiments reproduce or mimic the tactile sensations of the physical exam while providing accompanying dimensional references. As such, the calibration guide may provide a calibrated tactile point of reference for different cervical dilations.

Exemplary Embodiments

Figure 1:
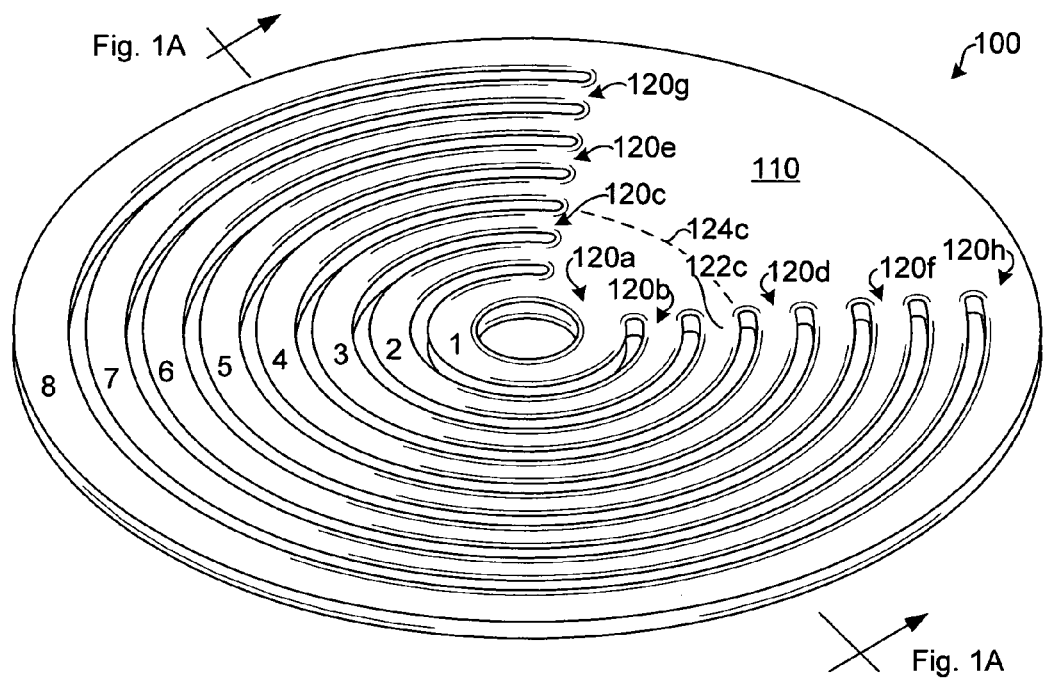
FIG. 1 illustrates a perspective view of a representation of an exemplary calibration guide in accordance with one embodiment of the inventive concepts.
Figure 1A:
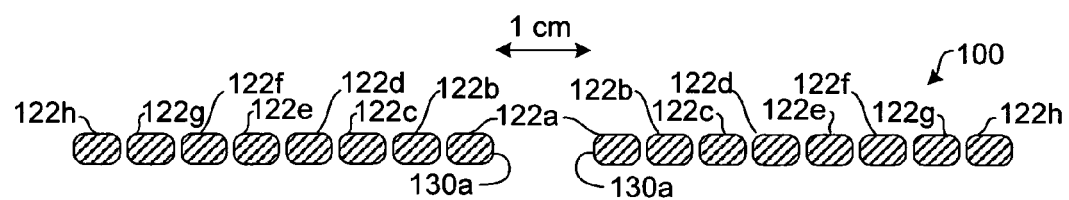
FIG. 1A illustrates a cross-sectional view of a representation of an exemplary calibration guide in accordance with one embodiment of the inventive concepts.
Figure 2:
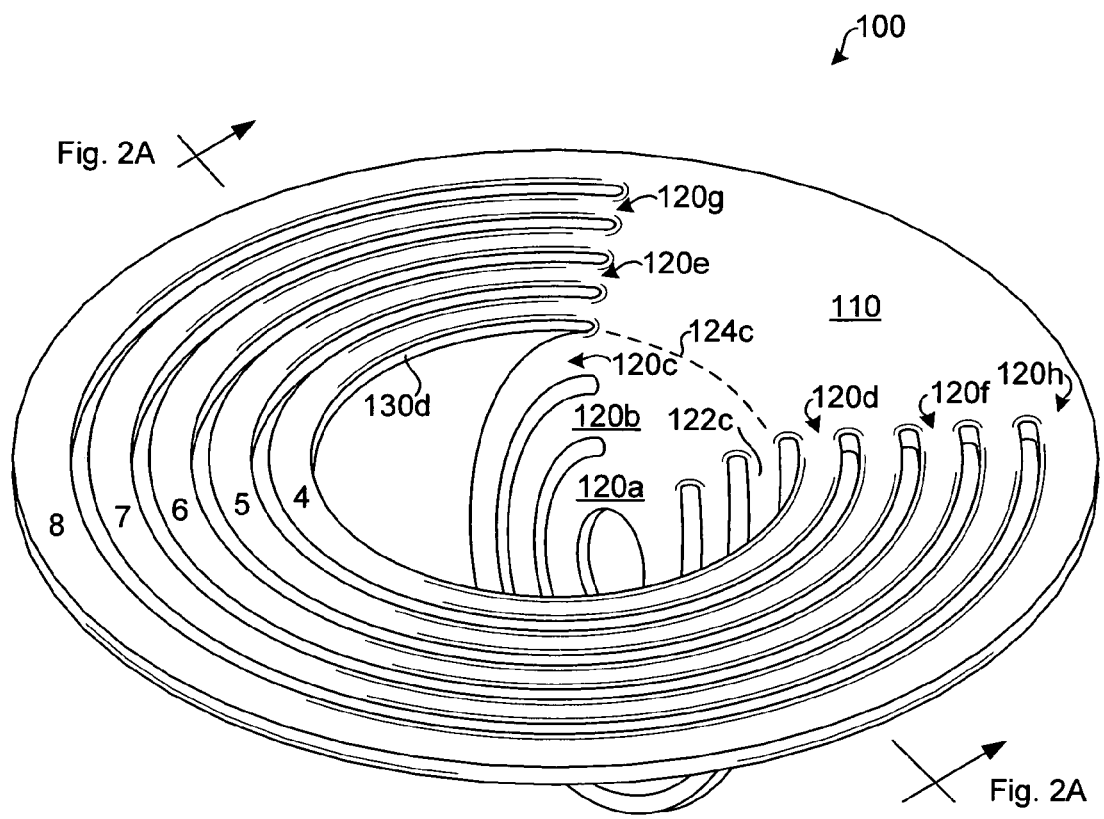
FIG. 2 illustrates a perspective view of a representation of an exemplary calibration guide in accordance with one embodiment of the inventive concepts.
Figure 2A:
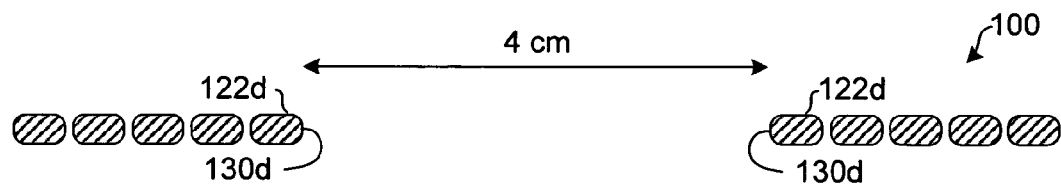
FIG. 2A illustrates a cross-sectional view of a representation of an exemplary calibration guide in accordance with one embodiment of the inventive concepts.

FIGS. 1–2A represent an exemplary calibration guide in accordance with one embodiment. FIGS. 1 and 2 illustrate perspective representations of calibration guide 100, while FIGS. 1A and 2A illustrate cross-sectional views of calibration guide 100.

In some embodiments, calibration guide 100 comprises a gripable structure 110 that is gripped by a caregiver and multiple reference structures to provide a tactile representation of the caregiver's most recent digital exam experience. In the particular embodiment illustrated in FIGS. 1–2A there are eight reference structures 120a–120h. As will become apparent below, other calibration guides can have more or fewer reference structures.

In some embodiments, individual reference structures can have a deflectable region and a hinge region. Such an example can be appreciated in relation to reference structure 120c which has deflectable region 122c and hinge region 124c as indicated in FIGS. 1 and 2. In some embodiments including this one, individual hinge regions can be joined with, and/or can comprise a portion of, gripable structure 110. In this particular embodiment the hinge regions are radially arranged about a central focus (not specifically designated) and along gripable structure 110.

Individual deflectable regions, such as deflectable regions 122a–122h, can be deflectable from a non-deflected position to a deflected position. For example, FIGS. 1–1A illustrate all the deflectable regions in the non-deflected position. FIGS. 2–2A illustrate deflectable regions 122a–122c in the deflected position with the remainder of the deflectable regions 122d–122h being in the non-deflected position. In this particular embodiment, calibration guide 100 is constructed of a resilient material which tends to assume a generally planar non-deflected configuration unless acted upon by a user.

In some embodiments, calibration guide 100 can comprise tactile reference surfaces which are located at calibrated distances from one another. For example as indicated in FIG. 1A, tactile reference surface 130a defines a distance of 1 centimeter (cm) therebetween. This distance is represented by the "1" mark on reference structure 120a as indicated in FIG. 1. As can be similarly evidenced from FIGS. 2–2A, tactile reference surface 130d is located on and defined by reference structure 120*d* and defines a distance of 4 cm extending therebetween. This 4 cm distance is indicated by the "4" mark indicated on reference structure 120*d* in FIG. 2. Other configurations are described below. The function of these calibrated tactile reference surfaces will become apparent below.

In this embodiment, the calibration guide's reference surfaces are located on an individual deflectable region. For example, as evidenced from FIG. 1A, tactile reference surfaces 130*a* are located on deflectable region 122*a*. Other configurations are described below in relation to FIGS. 7A–7C.

Reference structures can have various geometrical configurations. For example, in this illustrated embodiment reference structures 120*a*–120*h* are generally elliptical. In this particular embodiment, the reference structures approximate annuli and are generally flap-like. Further, in this particular embodiment reference structures 120*a*–120*h* are nested about one another. Examples of other configurations will be provided below.

Calibration guides can be formed from various materials. For example, polymers, or even paper may be utilized. Calibration guides can be of homogeneous construction or made from multiple materials. One exemplary formation process can utilize injection molding of a suitable polymer to form a calibration guide. The skilled artisan should recognize other suitable processes and materials. In some embodiments various surfaces of the calibration guide can be rounded or blended into one another to reduce regions where contamination may accumulate and/or to avoid damaging surgical gloves which may engage the surfaces.

Figure 3:
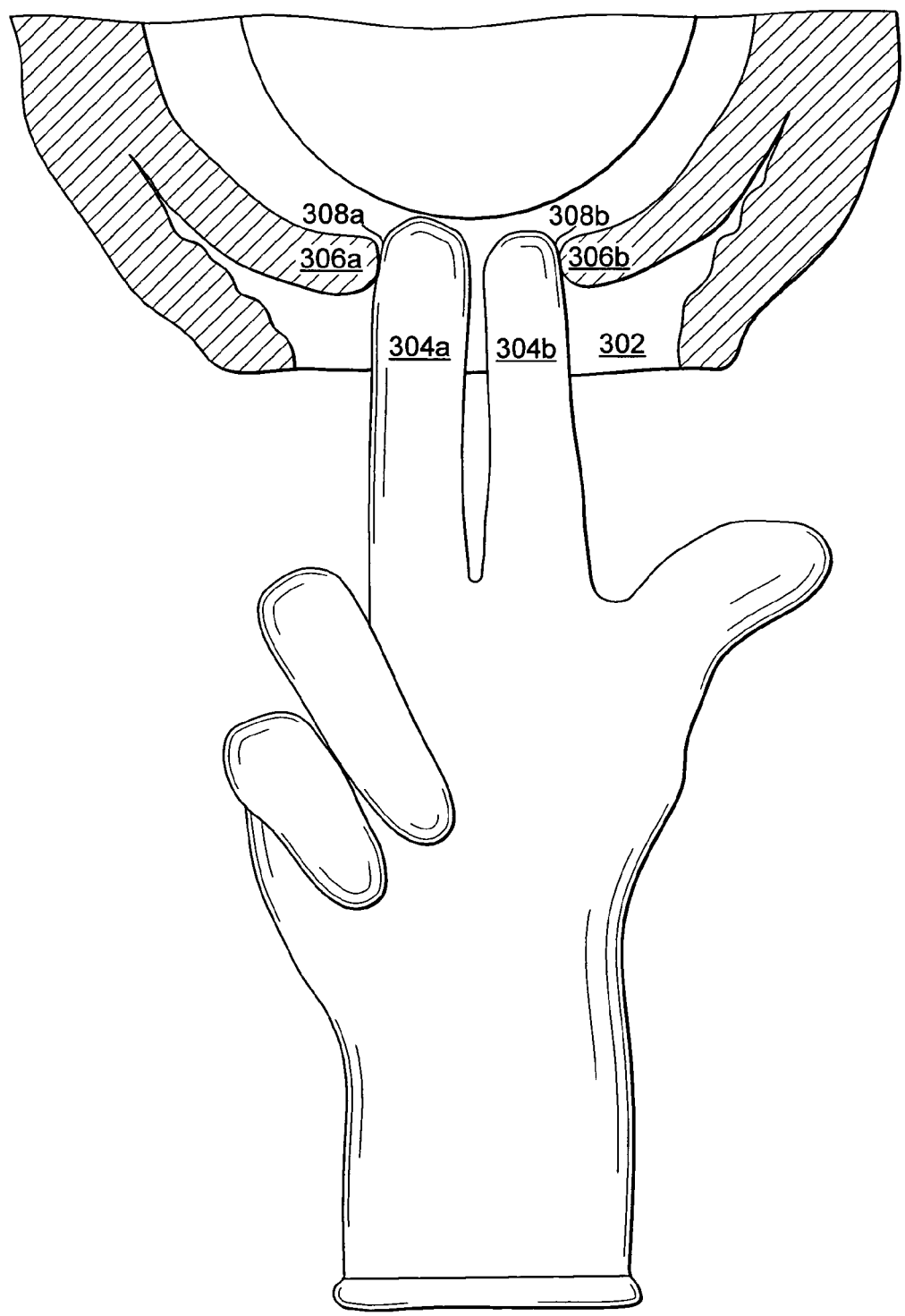
FIG. 3 illustrates a cross-sectional view of a representation of a patient's birth canal during a physical exam.
Figure 4:
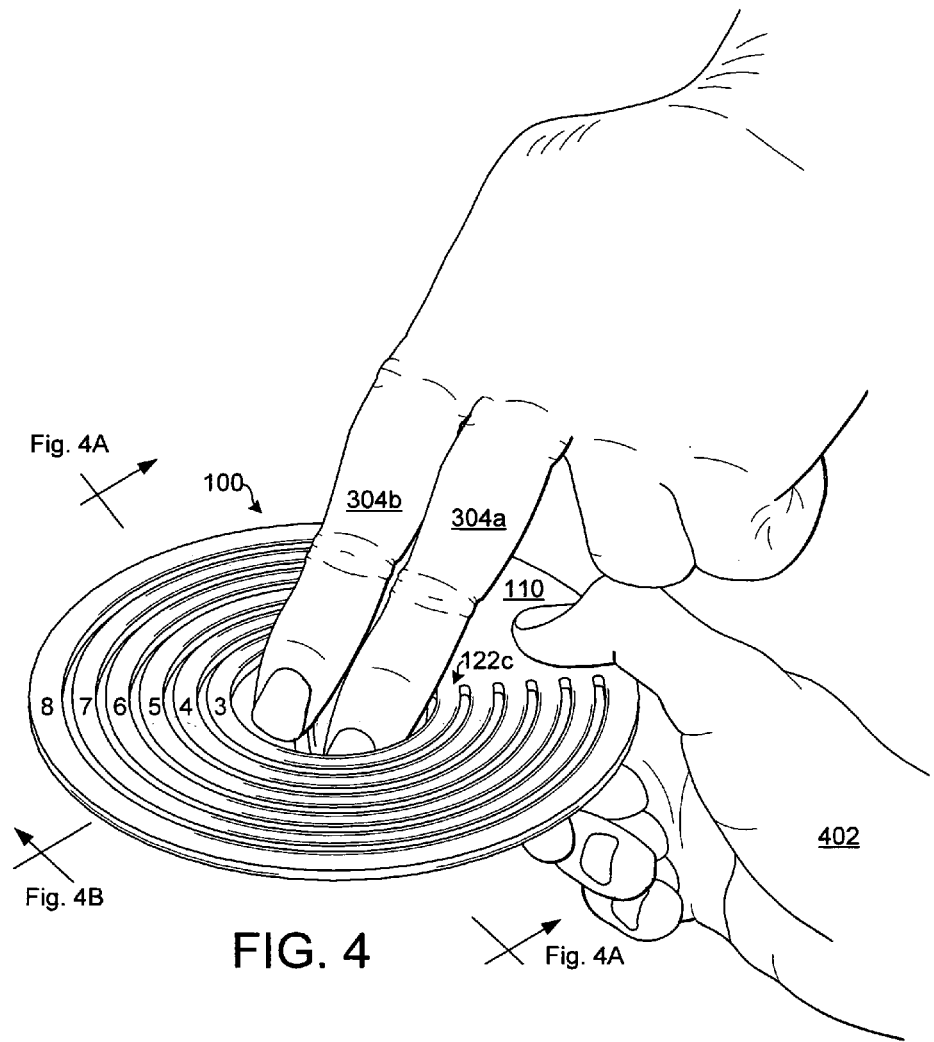
FIG. 4 illustrates a perspective view of a representation of an exemplary calibration guide engaged by a user in accordance with one embodiment of the inventive concepts.
Figure 4A:
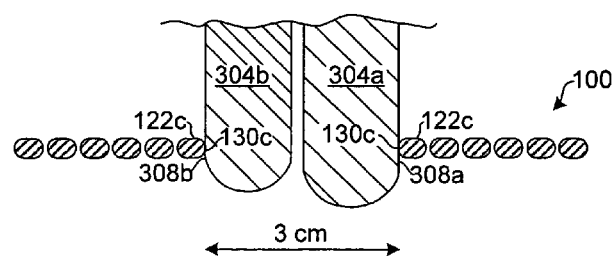
FIG. 4A illustrates a cross-sectional view of a representation of an exemplary calibration guide engaged by a user in accordance with one embodiment of the inventive concepts.
Figure 4B:
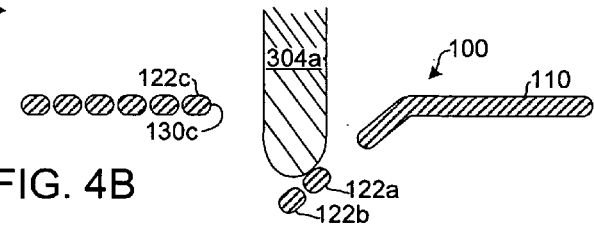
FIG. 4B illustrates a cross-sectional view of a representation of an exemplary calibration guide engaged by a user in accordance with one embodiment of the inventive concepts.

FIGS. 3–4B describe an exemplary process in which calibration guide 100 can be utilized.

FIG. 3 illustrates a basic representation of a digital pelvic exam. One or more fingers are inserted into birth canal 302. In this instance two digits or fingers 304*a*, 304*b* are utilized. Fingers 304*a*, 304*b* tactically engage generally opposing cervical rims 306*a*, 306*b*. Commonly the fingers' outer opposing surfaces 308*a*, 308*b* proximate the fingertips engage the cervical rims 306*a*, 306*b*. In such an exam the caregiver may not be able to see the cervical rims and may instead rely on the tactile sensations to determine the patient's physical condition.

FIG. 4 illustrates a perspective view and FIGS. 4A–4B illustrate cross-sectional views of calibration guide 100 engaged by the user or caregiver. FIG. 4 illustrates a representation of a user grasping calibration guide's gripable region 110 with a non-examining hand 402. Upon withdrawal of the examining hand from the birth canal, the examining fingers 304*a*, 304*b* can engage the reference structures 120*a*–120*h* which are specifically designated above in FIGS. 1–2.

As depicted in FIG. 4, the caregiver can engage individual reference structures with fingers 304*a*, 304*b* held at approximately the same orientation relative to one another as was experienced when contacting the cervical rims during the patient's physical exam.

In this process individual reference structures provide tactile points of reference to the caregiver. In some embodiments, the reference structures' generally opposing surfaces can reproduce or mimic the tactile stimulation experienced by the caregiver during the exam. For example, one or more of the reference structures' deflectable regions can deflect downward to allow fingers 304*a*, 304*b* to engage the tactile reference surfaces. In but one example, as illustrated in FIGS. 4 and 4B deflectable regions 122*a*, 122*b* are deflected downward exposing tactile reference surfaces 130*c* (designated FIG. 4A). If the caregiver perceives that a given tactile reference structure represents or mimics the tactile sensations of the patient's cervical exam then the appropriate reference numbers can provide the calibrated dimensions corresponding to the patient's cervical dilation. For example, if the caregiver determines that the tactile sensation illustrated in FIG. 4 mimics that experienced in FIG. 3, the caregiver can reference the associated reference number to determine the patient's dilation. The distance between generally opposing portions of tactile reference surfaces 130*c* is calibrated at "3" centimeters as indicated on reference structure 122*c*. Thus, in this example the calibration guide establishes or affirms that the patient's present dilation is approximately 3 cm.

Figure 5:
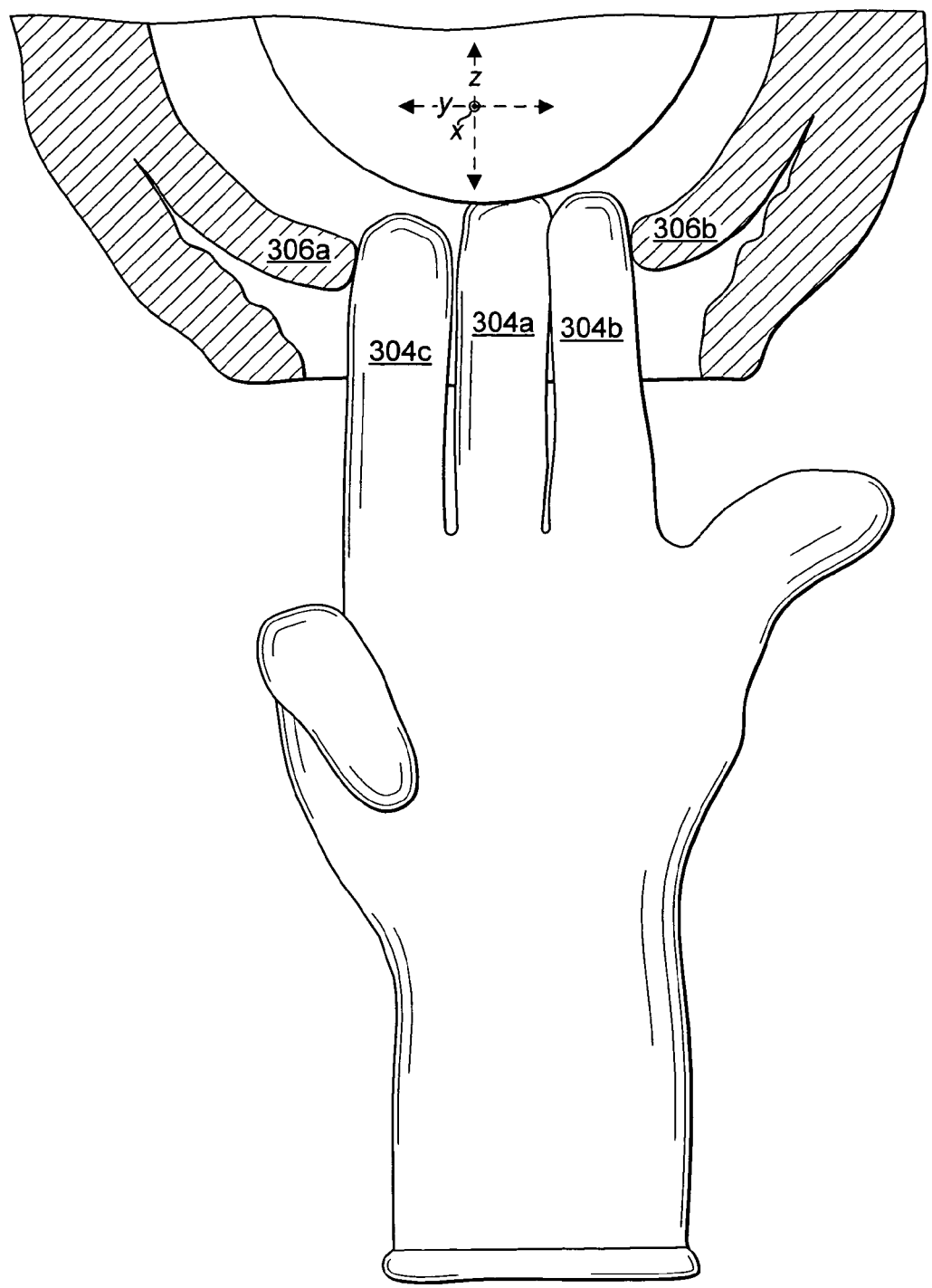
FIG. 5 illustrates a cross-sectional view of a representation of a patient's birth canal during a physical exam.
Figure 6:
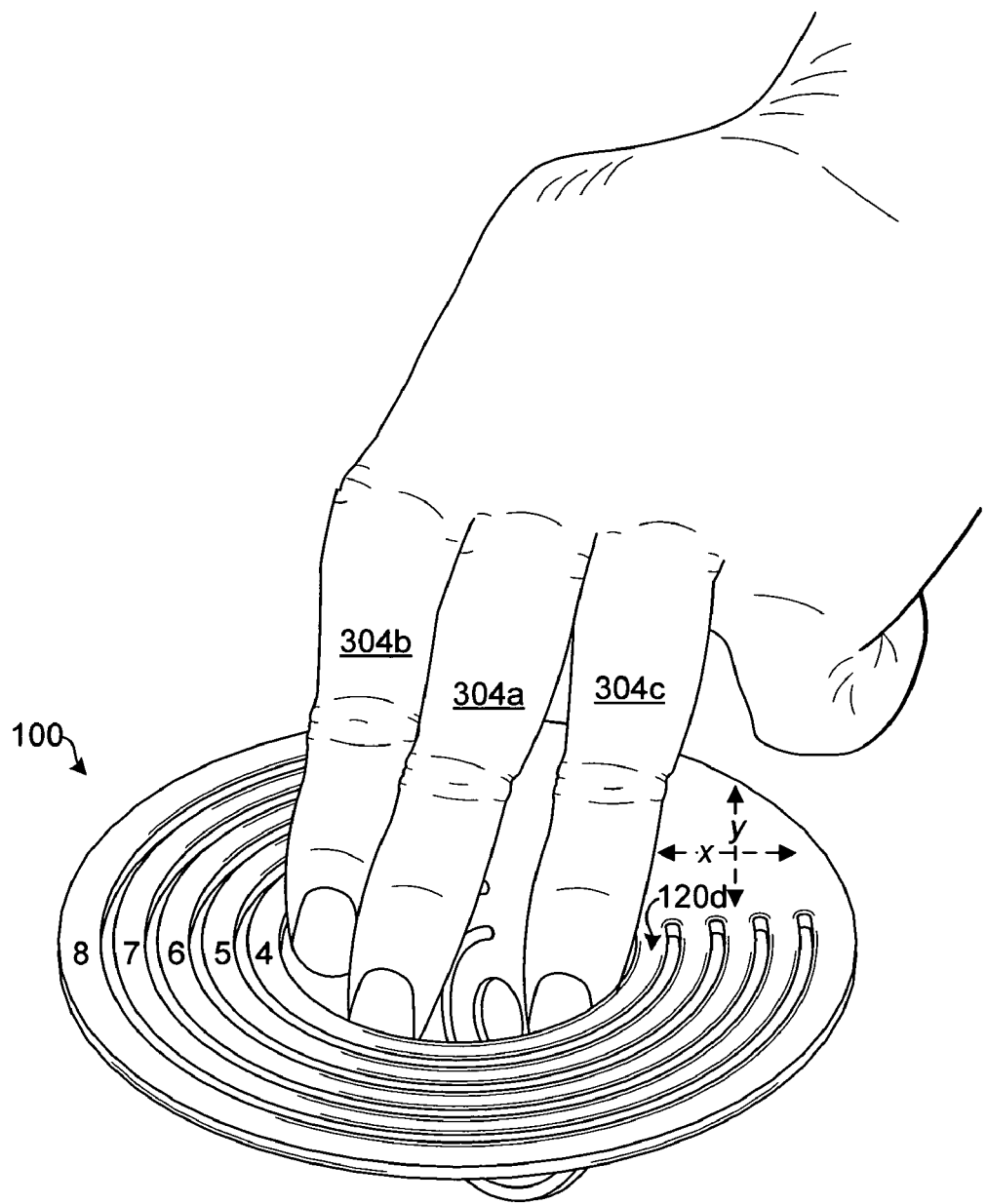
FIG. 6 illustrates a perspective view of a representation of an exemplary calibration guide engaged by a user in accordance with one embodiment of the inventive concepts.

FIGS. 5–6 provide still another illustrative example for using calibration guide 100. As illustrated in FIG. 5, a caregiver is conducting another physical exam. In this instance the caregiver is utilizing three digits 304*a*–304*c* to conduct the exam. Such an exam can allow the caregiver tactile sensation along two different axes, such as along the x- and y-axes as illustrated here. Upon completion of the physical exam, the caregiver can engage calibration guide 100 as represented in FIG. 6. The caregiver can engage the calibration guide such that the tactile sensation is similar to engaging the cervical rims 306*a*, 306*b* during the exam as illustrated in FIG. 5.

When the tactile sensation of calibration guide 100 mimics that experienced during the exam, the caregiver can consult the appropriate reference number to determine the patient's dilation. As illustrated in FIG. 6 the dilation is indicated by reference numeral "4" located in reference structure 120*d*. In this particular embodiment the "4" corresponds to 4 cm. Other embodiments may be calibrated to other units of measure such as inches.

Figure 7A:
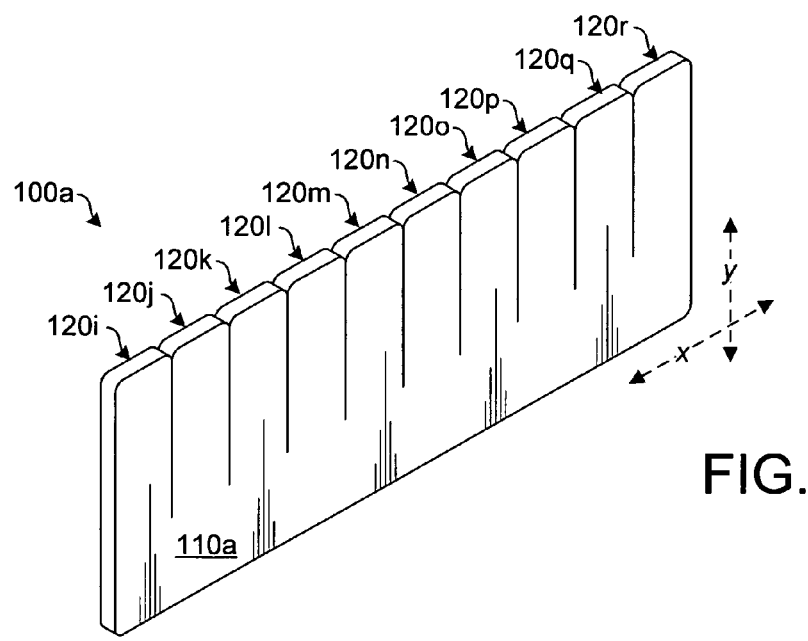
FIG. 7A illustrates a perspective view of a representation of an exemplary calibration guide in accordance with one embodiment of the inventive concepts.
Figure 7B:
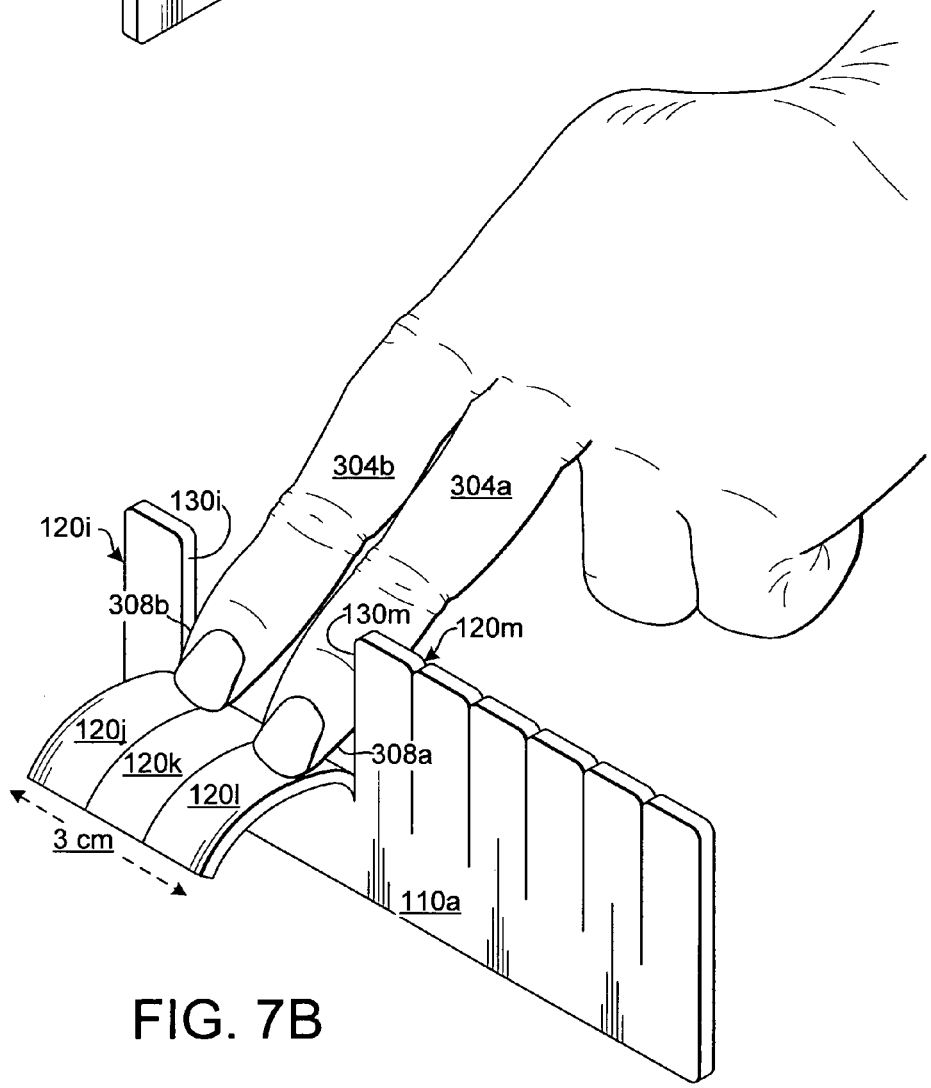
FIGS. 7B–7C illustrate perspective views of a representation of an exemplary calibration guide engaged by a user in accordance with one embodiment of the inventive concepts.
Figure 7C:
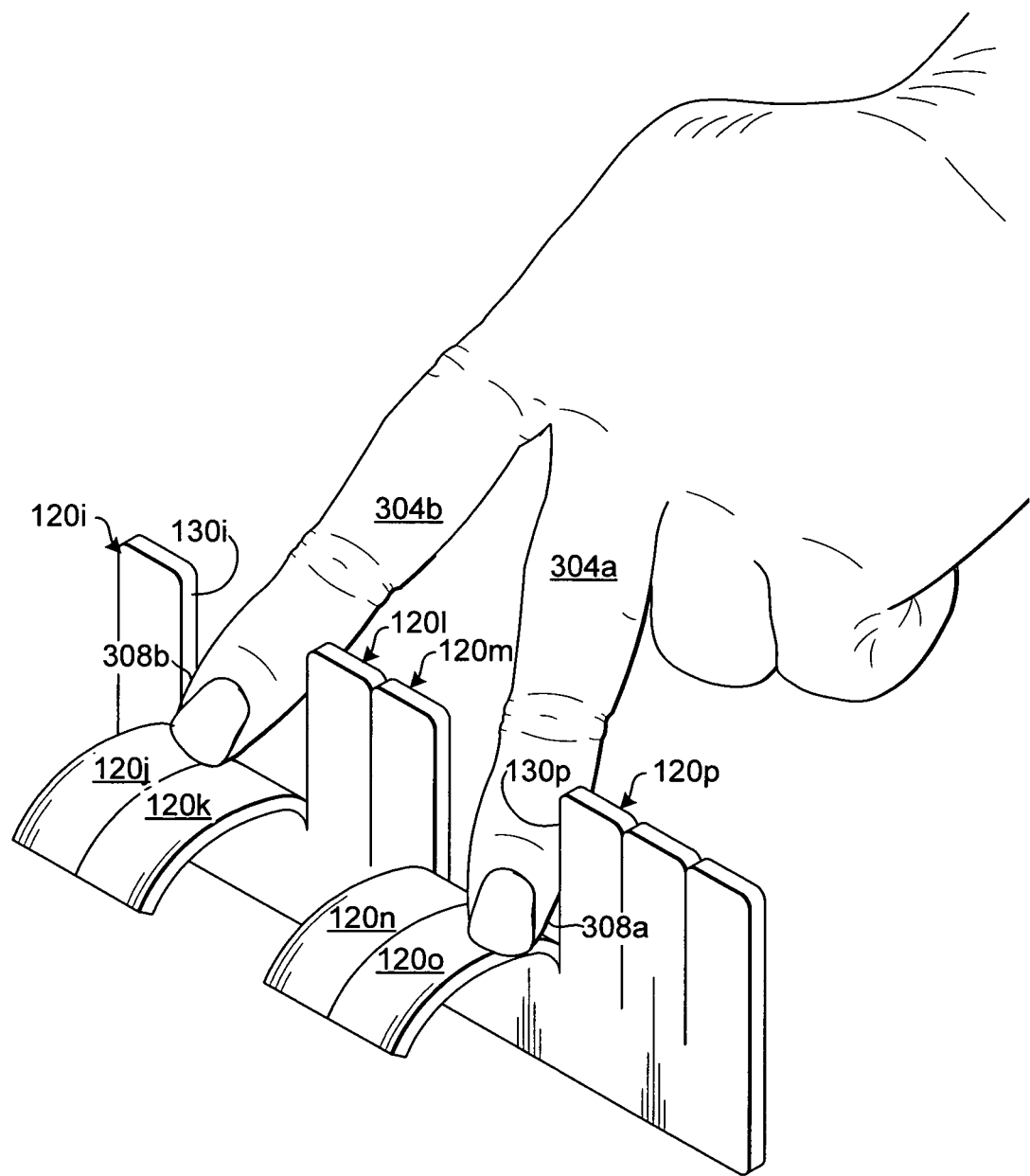

FIGS. 7A–7C illustrate another exemplary dilation guide 100*a*. In this particular embodiment gripable region 110*a* is elongate and extends generally along an axis; in this instance the x-axis. Reference regions 120*i*–120*r* extend away from gripable region 110*a* generally orthogonal the x-axis. In this embodiment individual reference regions are approximately 1 cm wide and are in physical contact with or slightly separated from adjacent gripable regions. After conducting a physical exam as for example described in relation to FIG. 2, a caregiver can engage calibration guide 100*a* as illustrated in FIG. 7B. Outer surfaces 308*a*, 308*b* of the caregivers fingers 304*a*, 304*b* respectively can tactically engage the calibration guide's tactile reference surfaces to mimic the patients cervical dilation. In the illustrated instance reference structures 120*j*–120*l* are deflected by the caregiver's fingers 304*a*, 304*b* to expose reference surfaces 130*i*, 130*m*. In this instance the reference surfaces, as illustrated, can define a distance of 3 cm therebetween. This configuration can establish or confirm the patient's dilation for the caregiver.

Figure 8:
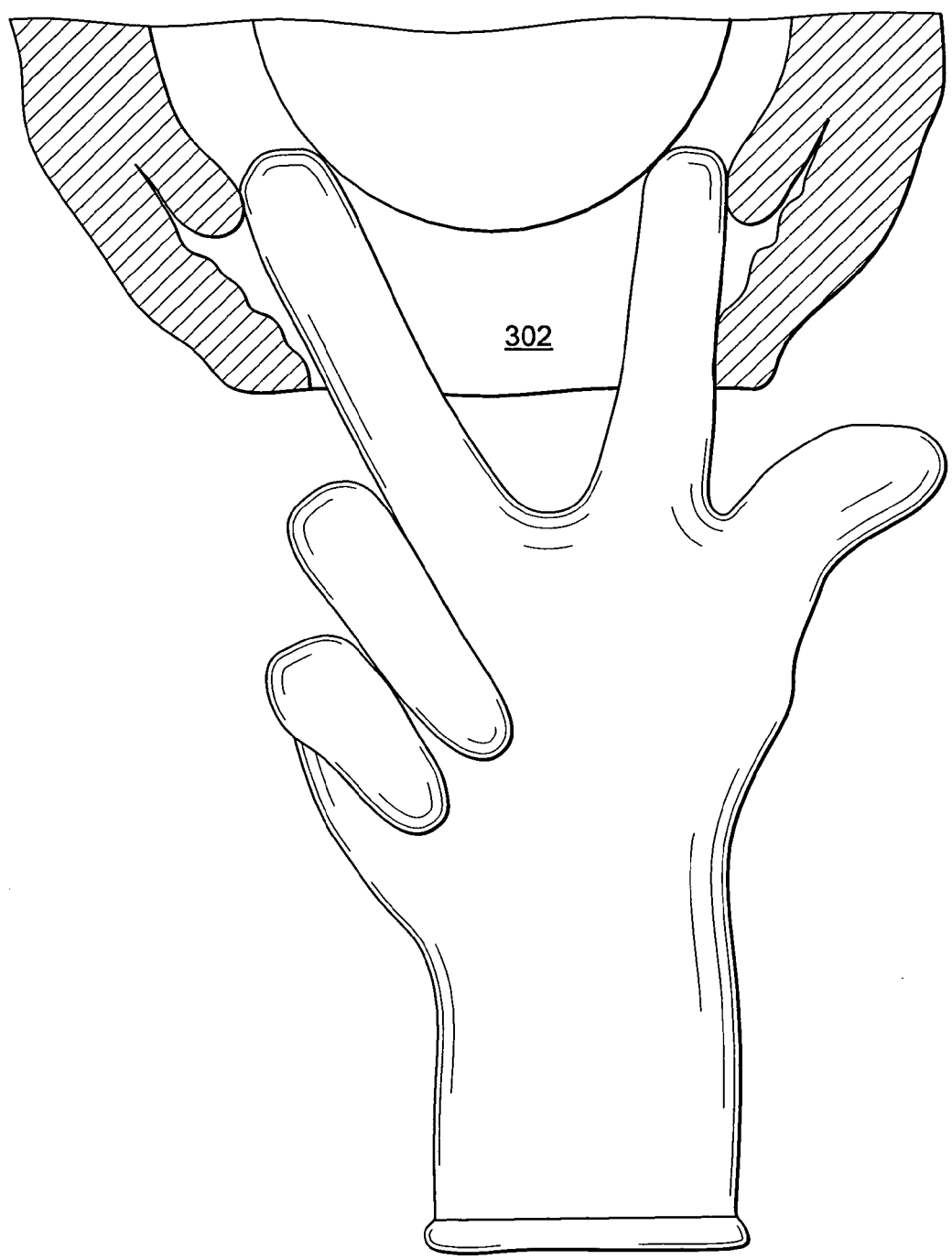
FIG. 8 illustrates a cross-sectional view of a representation of a patient's birth canal during a physical exam.

FIG. 8 illustrates another physical exam of birth canal 302 at a subsequent point in the delivery process where cervical dilation has increased relative to the dilation illustrated in FIGS. 3 and 5. FIG. 7C illustrates the caregiver's fingers engaging calibration guide 100*a* to determine the patient's dilation as illustrated in FIG. 8. In this instance the outer surfaces 308*a*, 308*b* of the caregiver's fingers 304*a*, 304*b* engage tactile reference surfaces 130*p* and 130*i* respectively. Tactile reference surfaces 130*i* and 130*p* in this embodiment are separated by 6 reference structures 120*j*–120*o* or 6 cm. In this particular configuration, reference structures 120*j*–120*k* are deflected by finger 304*b* to allow engagement of tactile reference surface 130*i*. Similarly, reference structures 120*n*–120*o* are deflected by finger 304*a* to allow engagement of tactile reference surface 130*p*. In this instance, interposed reference structures 120*l*–120*m* remain in the non-deflected configuration. The skilled artisan should recognize that this is but one possible configuration.

The skilled artisan should recognize many configurations and uses for calibration guides. For example, some calibration guides may be constructed inexpensively as to allow them to be "single-use" disposable items. Other configurations may be reusable and able to withstand washing with bleach or other compounds and/or being heat resistant to allow autoclaving. In such a scenario a labor and delivery caregiver may carry a calibration guide as ubiquitously as a stethoscope. Alternatively or additionally calibration guides may be utilized as training aides for training caregivers. For example, practicing with a calibration guide can help a novice caregiver to mentally visualize what the tactile sensations of a physical exam represent. Further still, practicing with a calibration guide may aid the novice caregiver to engage the cervical rims during an actual pelvic exam.

Figure 9:
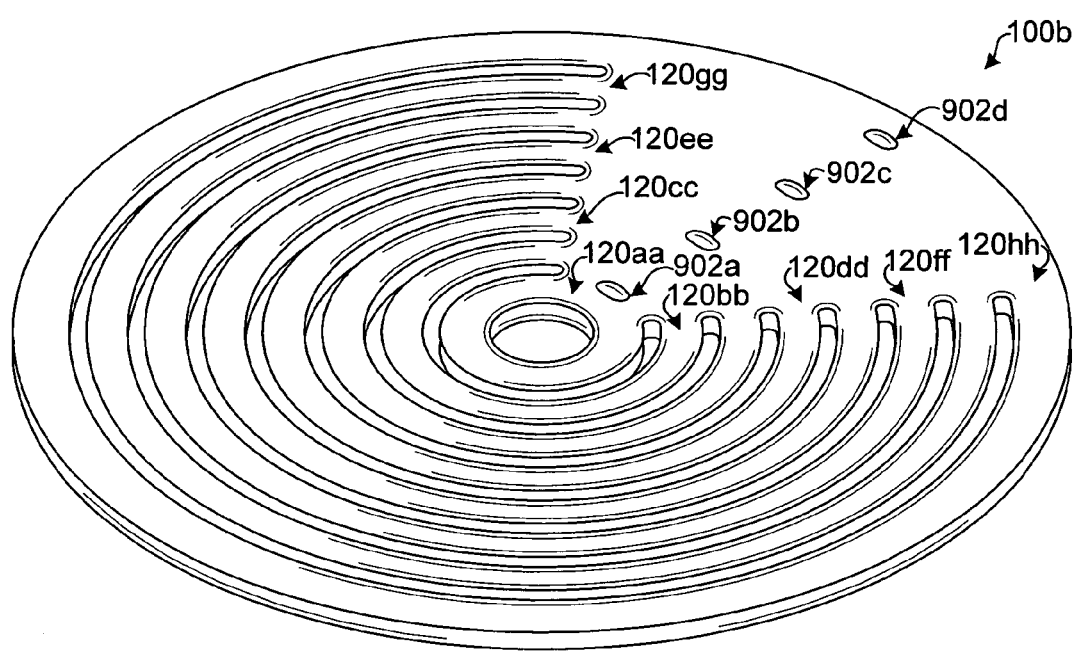
FIG. 9 illustrates a perspective view of a representation of an exemplary calibration guide in accordance with one embodiment of the inventive concepts.

Several exemplary calibration guide configurations are described above. FIG. 9 illustrates still another exemplary configuration where calibration guide 100b has a set of deployable reference structure 120aa–120hh and a second different set of reference structures 902a–902d. In this example, the second different set of reference structures 902a–902d are positioned at 1 cm increments and can be utilized in assessing the patient's effacement. In this particular configuration the caregiver can position their finger relative to the second set of reference structures to access the length of the cervix as it thins during the progression of labor. The skilled artisan should recognize other configurations.

CONCLUSION

Obstetric calibration guides for use in assessing physical measurements of a patient during pregnancy are described above. In some embodiments, the calibration guide can comprise a tactilely-resistant, cervix-approximating reference structure. Further, in some embodiments, the calibration guide may comprise a resilient digital dilation guide which is not configured to be inserted into the birth canal. The calibration guide can have deployable reference structures which comprise tactile reference surfaces. A caregiver can tactically engage these tactile reference surfaces to mimic the patient's cervical dilation. These reference surfaces can be at calibrated distances which can establish or confirm the patient's dilation for the caregiver.

Although the inventive concepts have been described in language specific to structural features and/or methodological steps, it is to be understood that the inventive concepts in the appended claims are not limited to the specific features or steps described. Rather, the specific features and steps are disclosed as forms of implementing the inventive concepts.

The invention claimed is:

1. A cervical calibration guide comprising:
    a gripable structure generally extending along a plane and configured to allow a user to grip the cervical calibration guide; and,
    a set of nested cervix-approximating reference structures that are coupled to but distinguishable from the grip able structure and which tend to generally lie in the plane with the gripable structure unless acted upon by one or more fingertips of a user, individual cervix-approximating reference structures of the set extending arcuately from a first portion of the gripable structure uninterruptedly along a majority of the cervical calibration guide when viewed orthogonal to the plane to a second opposite portion of the gripable structure effective to facilitate deflection of individual cervix-approximating reference structures out of the plane, the cervix-approximating reference structures collectively approximating calibrated instances of a progression of cervical dilation during delivery of a fetus.

2. The cervical calibration guide as recited in claim 1, wherein the cervix-approximating reference structures and the grip able structure comprise a same material.

3. The cervical calibration guide as recited in claim 1, wherein the cervix-approximating reference structures and the gripable structure comprise a polymer.

4. The cervical calibration guide as recited in claim 1, wherein individual cervix-approximating reference structures are generally annular.

5. The cervical calibration guide as recited in claim 1, wherein individual cervix-approximating reference structures are flap-like.

6. A method comprising:
    forming a cervical calibration guide that includes:
        a gripable structure generally extending along a plane and configured to allow a user to grip the cervical calibration guide; and,
        a set of nested cervix-approximating reference structures that are coupled to but distinguishable from the gripable structure and which tend to generally lie in the plane with the gripable structure unless acted upon by one or more fingertips of a user, individual cervix-approximating reference structures of the set extending arcuately from a first portion of the gripable structure uninterruptedly along a majority of the cervical calibration guide when viewed orthogonal to the plane to a second opposite portion of the gripable structure effective to facilitate deflection of individual cervix-approximating reference structures out of the plane, the cervix-approximating reference structures collectively approximating calibrated instances of a progression of cervical dilation during delivery of a fetus.

7. The method as recited in claim 6, wherein the forming comprises molding.

8. A method comprising:
    gripping a gripable structure extending generally along a plane; and,
    digitally engaging at least one of a set of nested cervix-approximating reference structures effective to deflect the at least one of the set from the plane, wherein the set of nested cervix-approximating reference structures are coupled to but distinguishable from the gripable structure, individual cervix-approximating reference structures of the set extending arcuately from a first portion of the gripable structure uninterruptedly along a majority of the cervical calibration guide when viewed orthogonal to the plane to a second opposite portion of the gripable structure.

9. A method comprising:
    engaging a patient's cervix with one or more fingertips of either a left or right hand during a patient examination;
    gripping, with the other of the left or right hand, a gripable structure that extends generally along a plane; and,
    deflecting, with the one or more fingertips, at least one of a set of nested cervix-approximating reference structures from the plane to determine a dilation of the cervix.

10. The method as recited in claim 9, wherein the deflecting exposes the fingertips to calibration surfaces of an outwardly positioned cervix-approximating reference structure that is calibrated to approximate a specific dilation measurement.

* * * * *